(12) United States Patent
Orlow et al.

(10) Patent No.: US 6,749,840 B2
(45) Date of Patent: Jun. 15, 2004

(54) INHIBITION OF PIGMENTATION BY INHIBITION OF FATTY ACID SYNTHASE

(75) Inventors: Seth J. Orlow, New York, NY (US); Andrea Hall, Astoria, NY (US)

(73) Assignee: New York University, New York, NY (US)

(*) Notice: Subject to any disclaimer, the term of this patent is extended or adjusted under 35 U.S.C. 154(b) by 0 days.

(21) Appl. No.: 10/137,632

(22) Filed: May 2, 2002

(65) Prior Publication Data

US 2002/0182156 A1 Dec. 5, 2002

Related U.S. Application Data

(60) Provisional application No. 60/288,263, filed on May 2, 2001.

(51) Int. Cl.[7] ............ A61K 7/135; A61K 7/00; A61K 31/40
(52) U.S. Cl. ............ 424/62; 424/400; 424/401; 514/410
(58) Field of Search ............ 424/62, 400, 401; 514/410

(56) References Cited

U.S. PATENT DOCUMENTS

| | | | |
|---|---|---|---|
| 5,539,132 A | 7/1996 | Royer et al. | 549/545 |
| 5,981,575 A | 11/1999 | Kuhajda et al. | 514/473 |
| 6,123,959 A | 9/2000 | Jones et al. | 424/450 |
| 6,132,740 A | 10/2000 | Hu | 424/401 |
| 6,139,854 A | 10/2000 | Kawato | 424/401 |

FOREIGN PATENT DOCUMENTS

WO    WO 99/64025    12/1999

OTHER PUBLICATIONS

Brilliant et al., "Anatomy of Pigment Cell Genes Acting at the Cellular Level," Physiology, Chapter 18, pp 217–229.
Kremer et al, "Thiolactomycin and Related Analogues as Novel Anti-mycobacterial Agents Targeting KasA and KasB Condensing Enzymes in Mycobacterium Tuberculosis," Journal of Biological Chemistry, vol. 275, No. 22, 2000, pp 16857–16864.
Morisaki et al., "Syntheses of Cerulenin and its Analogs. 1. Cerulenin and its Analogs with Modified Side Chain," Chem. Pharm. Bull., vol. 40, No. 11, 1992, pp 2945–2953.
Oishi et al., "Thiolactomycin, a New Antibiotic, I. Taxonomy of the Producing Organism, Fermentation and Biological Properties," Journal of Antibiotics, vol. XXXV, No. 4, pp 391–395.
Orlow, "The Biogenesis of Melanosomes," Physiology, Chapter 6, pp 97–106.
Riley, "Molecules in Focus: Melanin," Int. J. Biochem. Cell Biol., vol. 29, No. 11, 1997, pp 1235–1239.
Shimazawa et al., "Syntheses of Cerulenin and its Analogs, II. Synthesis and Biological Activity of dl–Carbacerulenin, a Carbocyclic Analog of Cerulenin," Chem. Pharm. Bull., vol. 40, No. 11, pp 2954–2957.
Wang et al., Total Synthesis of (+)-Thiolactomycin[1] Tetrahedron Letters, vol. 25, No. 46, 1984, pp 5243–5246.
Ando et al., "Correlation Between the Number of Melanosomes, Tyrosinase mRNA Levels, and Tyrosinase Activity . . . ," Journal of Cellular Physiology, vol. 163, 1995, pp 608–614.
Arimura et al., "Type Selective Inhibition of Microbial Fatty Acid Synthasees by Thiolactomycin," Arch Microbiol, vol. 160, 1993, pp 158–161.

*Primary Examiner*—Shelley A. Dodson
(74) *Attorney, Agent, or Firm*—Hale and Dorr LLP

(57) ABSTRACT

The invention provides novel methods and pharmaceutical compositions designed to decrease melanin production by inhibiting fatty acid synthase in a melanocyte, thereby lightening skin pigmentation.

11 Claims, 1 Drawing Sheet

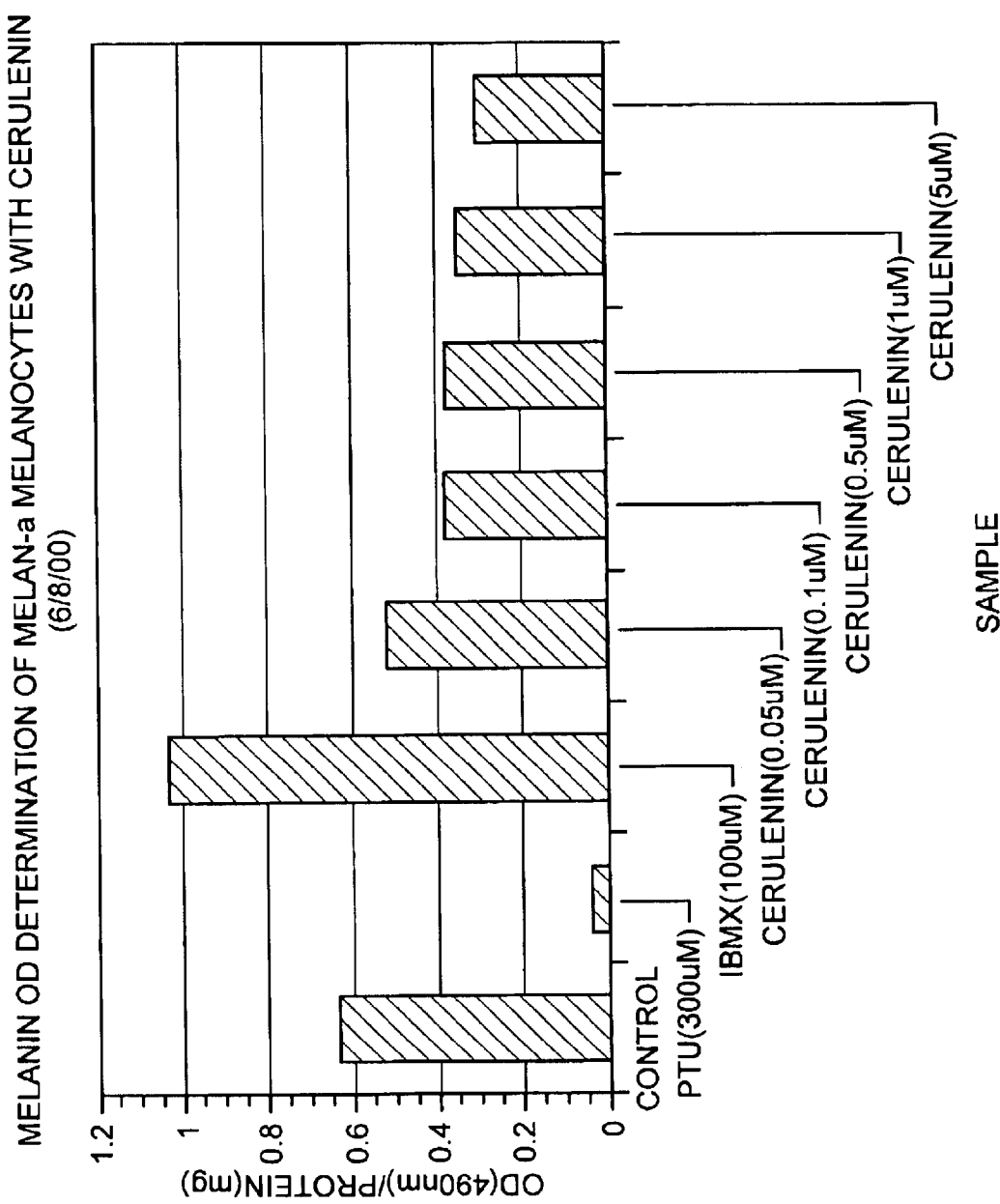

INHIBITION OF PIGMENTATION BY INHIBITION OF FATTY ACID SYNTHASE

CROSS-REFERENCE TO RELATED APPLICATIONS

This application claims priority to U.S. Provisional Application Serial No. 60/288,263, filed May 2, 2001, which are incorporated herein by reference in its entirety.

BACKGROUND OF THE INVENTION

1. Field of the Invention

The invention relates to the fields of medicine, pharmacology, biochemistry, and cell biology. More specifically, the invention relates to the fields of dermatology and cosmetics.

2. Description of the Related Art

Melanin is a dark pigment found in plants and animals that protects against ultraviolet radiation and provides decoration in the skin, eyes, hair, and fur of animals (reviewed in Riley (1997) Int. J. Biochem. Cell Biol. 11:1235–39). Melanocytes are cells of the epidermis specialized to produce melanin, which has two forms: brown/black eumelanin and yellow/red pheomelanin. A sophisticated intercellular signaling system determines whether an individual melanocyte will produce eumelanin or pheomelanin (reviewed by Brilliant and Barsh in The Pigmentary System: Physiology and Pathophysiology, Nordlund, et al. eds., (1998) Oxford University, New York, pp. 217–229).

Melanocytes synthesize melanin inside of specialized organelles called melanosomes (reviewed by Orlow in The Pigmentary System: Physiology and Pathophysiology, Nordlund, et al., eds., (1998) Oxford University, New York, pp. 97–106). These organelles are formed by the fusion of two types of vesicles. One type of vesicle, called a premelanosome, apparently derives directly from either the smooth endoplasmic reticulum or the trans-Golgi network. The other type of vesicle derives from the trans-Golgi network. Each of these types of vesicles contributes proteins to the melanosome necessary for its function.

For many individuals of all ages, the inappropriate production or overproduction of melanin is a serious cosmetic problem. By way of example, many children develop freckles after exposure to the sun, and for individuals in middle or advanced age, chloasma, freckles, and pigmentary deposits after sunburn tend to occur or increase in frequency. In addition, these pigment deposits do not disappear quickly and are more likely to become permanent with advancing age.

A number of products have been developed to effect a decrease in skin pigmentation. One such product contains hydroquinone, a well known active substance for skin de-pigmentation (e.g., see U.S. Pat. No. 6,139,854 to Kawato et al., issued Oct. 31, 2000). However, hydroquinone can have serious side effects if applied over a long period of time. For example, the application of hydroquinone to skin may lead to permanent de-pigmentation, and thus to increased photosensitivity of the skin when exposed to ultraviolet light. For that reason, in some countries hydroquinone is only allowed to be used for skin de-pigmentation in limited concentrations, and in other countries, the product is banned completely for this application.

A variety of other substances have been proposed for the control or inhibition of skin pigmentation. Almost all of these substances work by either bleaching existing pigment or preventing new pigment synthesis by inhibiting the activity of tyrosinase, the principle rate-limiting enzyme in the production of melanin. For example, U.S. Pat. No. 6,123,959 to Jones et al., issued Sep. 26, 2000, describes the use of aqueous compositions comprising liposomes of phospholipids, and at least one competitive inhibitor of an enzyme for the synthesis of melanin, in combination with at least one noncompetitive inhibitor of an enzyme for the synthesis of melanin. U.S. Pat. No. 6,132,740 to Lan Hu, issued Oct. 17, 2000, describes the use of certain resorcinol derivatives as skin lightening agents. WO 9964025A1 by Fytokem Products Inc., published Dec. 16, 1999, describes compositions for skin lightening which contain tyrosinase inhibiting extracts from dicotyledonous plant species indigenous to Canada. U.S. Pat. No. 5,580,549 to Fukada et al., issued Dec. 3, 1996, describes an external preparation for skin lightening comprising of 2-hydroxybenzoic acid derivatives and salts thereof as inhibitors of tyrosinase. WO 9909011A1 to Ostuka Pharmaceutical Co., Ltd., published Feb. 25, 1999, describes an agent for inhibiting skin erythema and/or skin pigmentation, containing at least one carbostyril derivative and salts thereof. U.S. Pat. No. 5,214,028 to Tomita et al., issued May 25, 1993, and U.S. Pat. No. 5,389,611 to Tomita et al., issued Feb. 14, 1995, describe lactoferrin hydrolyzates for use as a tyrosinase inhibitory agents.

Despite the development of these and other compositions to lighten skin, there remains a need in the art for the development of less toxic, safer alternatives to skin bleaching and more effective and efficient methods of inhibiting melanin production. The need for new and improved methods for lightening skin is evident in view of the cosmetic industry's estimate that the market for skin lighteners worldwide exceeds well over one billion dollars annually. Thus, there is a continuing need for the development of improved agents that limit or inhibit pigmentation in the skin.

SUMMARY OF THE INVENTION

It has surprisingly been discovered that various agents that inhibit fatty acid biosynthesis are useful for inhibiting melanin production. More specifically, it has been determined that agents capable of inhibiting fatty acid synthase (FAS) also inhibit the production of melanin in melanocytes. These discoveries have been utilized to provide the present invention, which includes methods and pharmaceutical compositions useful for decreasing skin pigmentation.

In one aspect, the invention provides a method of decreasing melanin synthesis in a melanocyte. The method comprises contacting the melanocyte with an FAS inhibitor, thereby reducing melanin synthesis in the melanocyte.

In another aspect, the invention provides a method of lightening skin, comprising contacting the skin of a patient in need thereof with a skin-lightening effective amount of an FAS inhibitor, thereby detectably reducing or inhibiting melanin synthesis and thereby lightening the skin.

The invention also provides, in another aspect, a composition for lightening skin, comprising a skin-lightening effective amount of an FAS inhibitor and a pharmaceutically acceptable carrier.

In another aspect, the present invention further provides a kit comprising a container comprising a composition comprising a skin-lightening effective amount of a compound that inhibits FAS activity. In one embodiment, the kit furthers comprises printed instructions as a label or a package insert directing the use of the pharmaceutical composition for lightening the skin.

In another aspect, the invention provides a method of making a pharmaceutical composition for lightening skin comprising combining a skin lightening effective amount of an FAS inhibitor with a pharmaceutical acceptable carrier.

In some embodiments, the FAS inhibitor is selected from the group consisting of cerulenin and a cerulenin analog, including pharmaceutically acceptable salts and solvates thereof. As used therewith, the term "analog" refers to a chemical compound that is structurally related to cerulenin and retains at least a measurable amount of FAS inhibitory activity. Non-limiting examples of cerulenin analogs include those described in Morisaki et al. (1992) *Chem. Pharm. Bull.* 40:2945–2953, Shimazawa et al. (1992) *Chem. Pharm. Bull.* 40:2954–2957, and U.S. Pat. No. 5,539,132 to Royer et al., issued Jul. 23, 1996. Cerulenin may be obtained commercially from Sigma (St. Louis, Mo.).

In some embodiments, the FAS inhibitor is selected from the group consisting of an α-methylene-γ-butyrolactone and an α-methylene-γ-butyrolactone analog, including pharmaceutically acceptable salts and solvates thereof. As used therewith, the term "analog" refers to a chemical compound that is structurally related to the respective α-methylene-γ-butyrolactone and retains at least a measurable amount of FAS inhibitory activity. Non-limiting examples of α-methylene-γ-butyrolactone analogs include those described in U.S. Pat. No. 5,981,575 to Kuhajda et al., issued Nov. 9, 1999. Alpha-methylene-γ-butyrolactone may be obtained commercially from Sigma (St. Louis, Mo.).

In some embodiments, the FAS inhibitor is selected from the group consisting of thiolactomycin and thiolactomycin analogs, including pharmaceutically acceptable salts and solvates thereof. As used therewith, the term "analog" refers to a chemical compound that is structurally related to thiolactomycin and retains at least a measurable amount of FAS inhibitory activity. Non-limiting examples of thiolactomycin analogs thereof are provided in Wang et al. (1984) *Tetrahdron Lett.* 25:5243–5246, Oishi et al. (1982) *J. Antibiotics* 35:391–395 (ATCC Strain No. 31319 disclosed therein), and Kremer et al. (2000) *J. Bio. Chem.* 275:16857–16864.

In other embodiments, the FAS inhibitor is triclosan or analogs thereof. Triclosan is known to inhibit enoyl-reductase of type I fatty acid synthase. In other embodiments, the inhibitors of FAS are 4-phenyl-5-phenylimino-[1,2,4] dithiazolidin-3-one) or 5-chloro-4-phenyl-[1,2]-dithiol-3-one).

BRIEF DESCRIPTION OF THE DRAWING

FIG. 1 is a graphic representation showing the effect of cerulenin on Melan-a melanocytes. Cells were treated with 300:9 phenyl-2-thiourea (PTU), with 100:9 isobutylmethylxanthine (IBMX), or with 0.05:9, 1:9, 0.5:9, or 5:9 cerulenin, or were untreated, as described in Example 1 below.

DETAILED DESCRIPTION

The patent and scientific literature referred to herein establishes knowledge that is available to those with skill in the art. The issued patents, applications, and references that are cited herein are hereby incorporated by reference to the same extent as if each was specifically and individually indicated to be incorporated by reference.

The invention provides methods and pharmaceutical compositions for inhibiting melanin production and skin pigmentation which comprise the use of agents that inhibit the activity of fatty acid synthase (FAS).

FAS (E.C. 2.3.1.85) is one of four major enzymes comprising the fatty acid biosynthetic pathway in humans. The fatty acid biosynthetic pathway components include: acetyl-CoA carboxylase, which is the rate limiting enzyme that synthesizes malonyl-CoA; malic enzyme, which produces NADPH; citrate lyase, which synthesizes acetyl-CoA; and FAS, which catalyzes NADPH-dependent synthesis of fatty acids from acetyl-CoA and malonyl-CoA. Free fatty acids, the final products of FAS activity, require separate enzymatic derivatization with coenzyme-A for incorporation into other products. In higher organisms FAS is a multifunctional enzyme which is well known to carry out the following seven enzymatic functions on a single molecule: acetyl transacylase, malonyl transacylase, β-ketoacyl synthetase (the condensing enzyme), β-hydroxyacyl reductase, β-hydroxyacyl dehydrase, enoyl reductase, and thioesterase (see Wakil (1989) *Biochem.* 28:4523–4530).

The present invention takes advantage of the discovery that the inhibition of the activity of FAS results in a decrease in melanin production in melanocytes. A connection between cholesterol synthesis and melanin production has been noted in the art (U.S. Pat. No. 6,126,947 to Savion et al., issued Oct. 3, 2000). It is also known that fatty acids are necessary substrates for intracellular esterfication of free cholesterol. Additionally, fatty acids are known to exert a regulatory effect on melanogenesis in melanoma by modifying the proteolytic degradation of tyrosinase (Ando et al. (1999) *J. Lipid Res.* 10:1312–1316). However, heretofore it was not known that the fatty acid biosynthetic pathway could affect melanogenesis.

Accordingly, in one aspect, the invention provides a method of decreasing melanin production in a melanocyte via the inhibition of FAS in the melanocyte.

The term "decreasing melanin production" is used herein to mean a detectable lowering of the amount of melanin synthesized de novo by a melanocyte exposed to a compound that inhibits FAS, as compared with the amount of melanin synthesized de novo by an untreated, control melanocyte. The term "lowering" preferably refers to about a 10% to about a 100% decrease in the amount of melanin synthesized de novo. More preferably, the term "lowering" refers to about a 25% to about a 100% decrease in the amount of melanin synthesized de novo. Most preferably, the term "lowering" refers to about a 50% to about a 100% decrease in the amount of melanin synthesized de novo.

The phrase "inhibiting the activity of FAS" is used herein to refer to about a 10% to about a 100% decrease in FAS activity. More preferably, the term "inhibiting the activity of FAS" refers to about a 25% to about a 100% decrease in FAS activity, and most preferably, to about a 50% to about a 100% decrease in FAS activity. The invention contemplates the inhibition FAS via any of the aforementioned seven enzymatic steps required for FAS activity and any inherent steps or processes. A decrease or change in FAS activity can be measured by any known method including, but not limited to, spectrophotometric methods based on the oxidation of NADPH, or methods involving the incorporation of radioactive or other labels into FAS substrates such as acetyl- or malonyl-CoA (Dils et al. (1975) *Meth. Enzymol.* 35:74–83).

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

"Inhibitors of FAS" include competitive and noncompetitive FAS inhibitors. A competitive FAS inhibitor is a molecule that binds the FAS enzyme in a manner that is mutually exclusive of substrate binding. Typically, a competitive inhibitor of FAS will bind to the active site. A noncompetive FAS inhibitor can be one which inhibits the synthesis of FAS, but its binding to the enzyme is not mutually exclusive over substrate binding. FAS inhibitors contemplated by this invention are compounds that reduce the activity of FAS in animal cells without any significant effect on other cellular activities, at least at comparable concentrations.

A wide variety of compounds have been shown to inhibit FAS, and selection of a suitable FAS inhibitor for use in this invention is within the skill of the ordinary worker in this art. Compounds which inhibit FAS can be identified by testing the ability of a compound to inhibit fatty acid synthase activity using purified FAS enzyme. For example, FAS synthase activity can be measured spectrophotometrically based on the oxidation of NADPH, or radioactively by measuring the incorporation of radiolabeled acetyl- or malonyl-CoA. (Dils et al., (1975) *Meth. Enzymol.* 35:74–83). FAS inhibitors are exemplified in, for example, International Patent Publication WO 94/02108 to The Johns Hopkins University, published Feb. 3, 1994. Suitable FAS inhibitors may also be identified by a simple test that uses a tumor cell line in which exposure to an FAS inhibitor is cytotoxic. Such cell lines include ZR-75-1 (ATCC No. CRL-1500) and preferably HL60 (ATCC No. CCL-240) (American Type Tissue Collection (ATCC), Manassas, Va.). Suitable FAS inhibitors will inhibit growth of such cell lines, but the cells are rescued by an exogenous supply of the fatty acid product of the FAS enzyme. When cell growth is measured in the presence and absence of exogenous fatty acid (e.g., palmitate or oleate), inhibition by the specific FAS inhibitor is relieved by the fatty acid.

By way of non-limiting example, cerulenin is one non-competitive FAS inhibitor useful in the methods of the invention. Structurally, cerulenin is characterized as [2R, 3S]-2,3-epoxy-4-oxo-7,10-trans, trans-dodecanoic acid amide. Cerulenin was originally isolated as a potential antifungal antibiotic from the culture broth of *Cephalosporium caerulens*. Its mechanism of action has been shown to be inhibition, through irreversible binding, of β-ketoacyl-ACP synthase, the condensing enzyme required for the biosynthesis of fatty acids (D'Agnolo et al. (1973) *Biochim. Biophys. Acta* 326:155–166). Cerulenin has been categorized as an antifungal, primarily against Candida and Saccharomyces species.

In some embodiments, the FAS inhibitor is selected from the group consisting of cerulenin and a cerulenin analog, including pharmaceutically acceptable salts and solvates thereof. As used herein, the term "analog" refers to a chemical compound that is structurally related to cerulenin and retains at least a measurable amount of FAS inhibitory activity. Non-limiting examples of cerulenin and cerulenein analogs include those described in Morisaki et al. (1992) *Chem. Pharm. Bull.* 40:2945–2953, Shimazawa et al. (1992) *Chem. Pharm. Bull.* 40:2954–2957, and U.S. Pat. No. 5,539,132 to Royer et al., issued Jul. 23, 1996. Alternatively, cerulenin may be obtained commercially from Sigma (St. Louis, Mo.).

In some embodiments, the FAS inhibitor is selected from the group consisting of an α-methylene-γ-butyrolactone and an α-methylene-γ-butyrolactone analog, including pharmaceutically acceptable salts and solvates thereof. As used herein, the term "analog" refers to a chemical compound that is structurally related to the respective α-methylene-γ-butyrolactone and retains at least a measurable amount of FAS inhibitory activity. Non-limiting examples of α-methylene-γ-butyrolactone analogs include those described in U.S. Pat. No. 5,981,575 to Kuhajda et al., issued Nov. 9, 1999. Alternatively, α-methylene-γ-butyrolactone may be obtained commercially from Sigma (St. Louis, Mo.).

In some embodiments, the FAS inhibitor is selected from the group consisting of thiolactomycin and thiolactomycin analogs, including pharmaceutically acceptable salts and solvates thereof. As used herewith, the term "analog" refers to a chemical compound that is structurally related to thiolactomycin and retains at least a measurable amount of FAS inhibitory activity. Non-limiting examples of thiolactomycin and analogs thereof are provided in Wang et al. (1984) *Tetrahdron Lett.* 25:5243–5246, Oishi et al. (1982) *J. Antibiotics* 35:391–395 (ATCC Strain No. 31319 disclosed therein), and Kremer et al. (2000) *J. Bio. Chem.* 275:16857–16864.

In other embodiments, the FAS inhibitor is triclosan or analogs thereof. Triclosan is known to inhibit enoyl-reductase of type I fatty acid synthase (Lui et al. *Cancer Chemother. Pharmacol.* 49:187–193 (2002). In other embodiments, the inhibitors of FAS are 4-phenyl-5-phenylimino-[1,2,4] dithiazolidin-3-one) or 5-chloro-4-phenyl-[1,2]-dithiol-3-one) (He et al. *Antimicorbial Agents and Chemotherapy* 46:1310–1318 (2002)).

Suitable FAS inhibitors can be characterized by a high therapeutic index. For example, inhibitors can be characterized by the concentration required to inhibit fatty acid synthesis in cell culture by 50% ($IC_{50}$ or $ID_{50}$). FAS inhibitors with high therapeutic indexes will inhibit fatty acid synthesis at a lower concentration (as measured by $IC_{50}$) than the $IC_{50}$ for inhibition of cell growth in the presence of exogenous fatty acid. Inhibitors whose effects on these two cellular activities show greater differences are more preferred. A preferred inhibitor of fatty acid synthesis will have an $IC_{50}$ for fatty acid synthetic activity that is at least one log lower, more preferably at least two logs lower, and even more preferably at least three logs lower than the inhibitor's $IC_{50}$ determined for cell growth.

Another way to determine if an FAS inhibitor is useful in the methods of the invention is to use any assay known to those with skill in the art which can demonstrate a reduction in melanogenesis. For example, cultured melanocytes can be incubated with a proposed FAS inhibitor test compound and tested for melanin content, e.g., spectrophotometrically, as described in Example 1 below. This melanin content is then compared with the melanin content of untreated, cultured melanocytes to determine if the FAS inhibitor inhibits melanogenesis.

In a non-limiting example, melanogenesis may be assayed in human primary melanocytes. Briefly, a test compound is incubated with human primary melanocytes in the presence of α-melanocyte stimulating hormone (α-MSH) for 2–3 days. Cells are then lysed with sodium hydroxide and sodium dodecyl sulfate (SDS) and melanin signals are read spetrophotometrically at 405 nm. Alternatively, $^{14}$C-DOPA is added to the cells in combination with the test compound and acid-insoluble $^{14}$C-melanin may be quantitated by a scintillation counter. The calculated $IC_{50}$ value reflects the inhibitory potency of the compound in the new melanin synthesis that was stimulated by α-MSH. A melanogenesis assay can also be performed with a human skin equivalent model. Briefly, a mixture of human melanocytes and keratinocytes is grown in an air-liquid interphase. This tissue culture forms a three-dimensional structure that histologically and microscopically resembles the human skin epidermis. A test compound is added on top of the cells to mimic topical drug application. After incubation with the compounds, the cells are washed extensively and lysed for DOPA oxidase assay.

Melanogenesis may also be examined in vivo. Briefly, black or dark brown guinea pigs with homogeneous skin color can be used in this type of study. A solution of the test compound (e.g., 1–5% in ethanol:propylene glycol, 70:30) and the vehicle control are applied to the skin of the animals twice daily, 5 days per week for 4–8 weeks. Using this assay, for example, depigmentation of the skin may be observed.

As detailed in U.S. Pat. No. 5,759,837 to Kuhajda et al., issued Jun. 2, 1998, other non-limiting representative inhibitors of FAS useful for the invention herein include: 1,3-dibromopropanone, Ellman's reagent [5,5'-dithiobis(2-nitrobenzoic acid), DTNB], 4-(4'-chlorobenzyloxy) benzyl nicotinate (KCD-232), 4-(4'-chlorobenzyloxy) benzoic acid (MII), 2[5(4-chlorophenyl)pentyl]oxirane-2-carboxylate (POCA) and its CoA derivative, ethoxyformic anhydride, thiolactomycin, phenyocerulenin, melarsoprol, iodoacetate, phenylarsineoxide, pentostam, melittin, methyl malonyl CoA, and FAS-inhibitory analogs thereof.

The present invention also relates to the use of pharmaceutically acceptable acid addition and base salts of any of the aforementioned compounds. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (i.e., 1,1-methylene-bis-(2-hydroxy-3-naphthoate)) salts.

The compounds useful according to the invention that are basic in nature are capable of forming a wide variety of different salts with various inorganic and organic acids. Although such salts must be pharmaceutically acceptable for administration to animals, it is often desirable in practice to initially isolate a compound from the reaction mixture as a pharmaceutically unacceptable salt and then simply convert the latter back to the free base compound by treatment with an alkaline reagent, and subsequently convert the latter free base to a pharmaceutically acceptable acid addition salt. The acid addition salts of the active base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

Those compounds useful according to the invention that are acidic in nature are capable of forming base salts with various pharmaceutically acceptable cations. Examples of such salts include the alkali metal and alkaline earth metal salts and, particularly, the sodium and potassium salts. These salts can be prepared by conventional techniques. The chemical bases that are used as reagents to prepare the pharmaceutically acceptable base salts of this invention are those that form non-toxic base salts with the acidic compounds of the invention. Such non-toxic base salts include those derived from such pharmaceutically acceptable cations as sodium, potassium, calcium and magnesium, etc. These salts can easily be prepared by treating the corresponding acidic compounds with an aqueous solution containing the desired pharmaceutically acceptable cations, and then evaporating the resulting solution to dryness, preferably under reduced pressure. Alternatively, they can be prepared by mixing lower alkanolic solutions of the acidic compounds and the desired alkali metal alkoxide together, and then evaporating the resulting solution to dryness, as described above. In either case, stoichiometric quantities of reagents are preferably employed in order to ensure completeness of reaction and maximum yields of the desired final products.

While the FAS inhibitors discussed herein are typically small molecule compounds that directly inhibit the enzyme, it will be readily apparent to the skilled clinician that specific prevention of FAS biosynthesis is an equivalent procedure which will accomplish the same desired result. Therefore, this invention also contemplates inhibition of FAS biosynthesis as a method for inhibiting melanogenesis or lightening skin. This may be accomplished by selectively degrading mRNA encoding FAS or otherwise interfering with its transcription and/or translation. This may be accomplished, for instance, by introduction of a ribozyme specific for FAS mRNA (see, e.g., Czubayko et al. (1994) *J. Biol. Chem.* 269:21358–21363 for ribozyme methodology). This may alternatively be accomplished by antisense RNA complementary to the nucleic acid sequence of FAS. The sequence of human FAS cDNA is deposited with GenBank (GenBank No. NM_004104). In one embodiment, antisense therapy involves an expression vector containing at least a portion of the sequence encoding human FAS operably linked to a promoter such that it will be expressed in antisense orientation. In another embodiment, an antisense sequence is designed with the knowledge of the known FAS sequence and synthesized chemically. In either case, the antisense molecules may be produced in a fashion in which the molecules are degradation resistant. Such modifications include a modified backbone, a cap structure, or any other modification known to those in the art that prevents degradation. As a result, antisense molecules complementary to and capable of binding or hybridizing to FAS mRNA will be produced. Upon binding to FAS mRNA, translation of that mRNA is prevented, and consequently FAS is not produced. Production and use of antisense expression vectors is described in more detail in U.S. Pat. No. 5,107,065 to Shewmaker et al., issued Apr. 21, 1992, and U.S. Pat. No. 5,190,931 to Masayori Inouye, issued Mar. 2, 1993.

The inhibition of FAS in melanocytes, and the subsequent inhibition or decrease in melanin synthesis that occurs as a result thereof, are useful in methods designed to lighten the skin. Thus, contact of melanocytes, either in vitro or in vivo, with an amount of an inhibitor of FAS that is effective to inhibit melanin production, will result in the desired skin lightening effect. Suitable compounds for this purpose include those described above for inhibiting FAS activity and include, but are not limited to, cerulenin and FAS-inhibitory analogs thereof, an (α-methylene-(α-butyrolactone and FAS-inhibitory analogs thereof, and thiolactomycin and FAS-inhibitory analogs thereof.

The term "lightening skin" is meant herein to refer to any detectable reduction in skin pigmentation, e.g., a reduction visible to the naked eye, that occurs after contacting the skin of an individual with a treatment regimen comprising an inhibitor of FAS.

Preferably, the methods and compositions of the invention are for application to a vertebrate cell or individual, more particularly to a mammalian cell or individual, and most preferably to a human cell or individual. The term "individual" is used herein to refer to a vertebrate, a mammal or a human.

For pharmaceutical and cosmetic uses, it is preferred that a compound that reduces skin pigmentation by inhibiting the activity of FAS in a melanocyte of the skin be part of a pharmaceutical composition. Pharmaceutical compositions of the invention may be administered to a human or animal having a disease, disorder, or condition which is of a type that causes the mis-production and/or the over-production of melanin.

In addition to pharmaceutical uses, the compositions and methods of the current invention are useful for cosmetic purposes. For example, occurrences in the skin or hair of noticeable but undesired pigmentation as a result of melanin production or overproduction may be treated using the methods of the present invention. Cosmetic applications for methods of the present invention include the application of compositions containing one or more compounds that decreases melanin production in a melanocyte by inhibiting FAS in the melanocyte to enhance or otherwise alter the visual appearance of skin or hair. Alternatively, the prevention of melanin production, for example as a result of sun or ultraviolet light exposure, is also contemplated as an appropriate application of the skin-lightening methods of the invention.

As used herein, the term "a person in need thereof" refers to an individual with a noticeable but undesired pigmentation condition or an individual that elects to decrease pigmentation in the absence of a noticeable and undesired pigmentation condition.

As one skilled in the art will be aware in view of the disclosure, the compositions used in the methods of the invention disclosed herein may be used alone or in combination with each other to inhibit FAS activity. Moreover, the methods of the invention also include the additional use of other compounds known in the art to inhibit melanin synthesis. For example, the compounds of the invention may be used in combination with an inhibitor of tyrosinase, which is an important enzyme in the synthesis of melanin. Such inhibitors are known to those skilled in the art (see, e.g., U.S. Pat. No. 5,580,549 to Fukada et al., issued Dec. 3, 1996). Alternatively, or additionally, skin bleaching compounds such as hydroquinones may be included in the composition.

The pharmaceutical compositions of the invention are administered to a subject such as a human or animal. Preferably, administration is by topical application. The compositions of the present invention may be in any of a variety of forms common in the pharmaceutical or cosmetic arts for topical application, including solutions, gels, lotions, ointments, creams, suspensions, pastes, liniments, powders, tinctures, aerosols, transdermal drug delivery systems or salves. Preferred ingredients include viscosity enhancing agents, pH stabilizers, antioxidants, stabilizers, perfumes and colorants. In one embodiment, formulations are those that are viscous enough to remain on the treated area, do not readily evaporate, and are easily removed by rinsing with water, optionally with the aid of soaps, cleansers and/or shampoos. In another embodiment, the invention includes formulations that are not easily removed by rinsing with water or washing with the aid of soaps, cleaners and/or shampoos. Actual methods for preparing topical formulations are known or apparent to those skilled in the art, and are described in detail in *Remington's Pharmaceutical Sciences* 17th ed., (1990) Mack Publishing Company, Easton, Pa.; and *Pharmaceutical Dosage Forms and Drug Delivery Systems,* 6th ed., Williams & Wilkins (1995).

In order to enhance the percutaneous absorption of the active ingredients, one or more of a number of agents may be added in the topical formulations including, but not limited to, dimethylsulfoxide, dimethylacetamide, dimethylformamide, surfactants, azone, alcohol, acetone, propylene glycol and polyethylene glycol. In addition, physical methods can also be used to enhance transdermal penetration such as, e.g., by iontophoresis or sonophoresis. Alternatively, or in addition, liposomes may be employed.

The compounds useful according to the invention (i.e., FAS inhibitors), and their pharmaceutically acceptable salts, are useful in the treatment of disorders of human pigmentation. The compounds useful according the invention are included in formulations of the invention at about 0.01% to about 50% by weight, or more preferably at about 0.1% to about 10% by weight, or most preferably at about 0.5% to about 5% by weight.

As used herein, a "skin-lightening effective amount" of a compound means an amount of the compound that detectably lightens skin after a therapeutically effective period of time. One skilled in the art is able to determine a "therapeutically effective period time" based on the particular diagnosis and the skin-lightening effect desired. Non-limiting examples of human pigmentation disorders include solar and simple lentigines (including age/liver spots), melasma/chloasma and postinflammatory hyperpigmentation. Such compounds reduce skin melanin levels by inhibiting the production of melanin, whether the latter is produced constitutively or in response to UV irradiation (such as sun exposure). Thus, some of the active compounds used in this invention can be used to reduce skin melanin content in non-pathological states so as to induce a lighter skin tone, as desired by the user, or to prevent melanin accumulation in skin that has been exposed to UV irradiation. They can also be used in combination with skin peeling agents (including glycolic acid or trichloroacetic acid face peels) to lighten skin tone and prevent repigmentation.

The invention relates both to methods of modulating the pigmentation of skin in which the FAS inhibitor, or a pharmaceutically acceptable salt thereof, and one or more of the other active ingredients referred to herein are administered together as part of the same pharmaceutical composition, as well as methods in which they are administered separately as part of an appropriate dose regimen designed to obtain the benefits of the combination therapy. The appropriate dose regimen, the amount of each dose administered, and specific intervals between doses of each active agent will depend upon the specific combination of active agents employed, the condition of the patient being treated, and the nature and severity of the disorder or condition being treated. Such additional active ingredients will generally be administered in amounts less than or equal to those for which they are effective as single topical therapeutic agents. The FDA approved dosages for such active agents that have received FDA approval for administration to humans are publicly available.

For example, any of the compounds used according to a skin-lightening method of the invention may be used in combination with a tyrosinase inhibitor or other skin-whitening agent as currently known in the art or to be developed in the future, including any one or more of those agents described in the following patent publications: U.S. Pat. No. 4,278,656 to Nagai et al, issued Jul. 14, 1981; U.S. Pat. No. 4,369,174 to Nagai et al., issued Jan. 18, 1983; U.S.

Pat. No. 4,959,393 to Torihara et al., issued Sep. 25, 1990; U.S. Pat. No. 5,580,549 to Fukuda et al., issued Dec. 3, 1996; U.S. Pat. No. 6,123,959 to Jones et al., issued Sep. 26, 2000; U.S. Pat. No. 6,132,740 to Hu, issued Oct. 17, 2000; U.S. Pat. No. 6,159,482 to Tuloup et al., issued Dec. 12, 2000; WO 99/32077 by L'Oreal, published Jul. 1, 1999; WO 99/64025 by Fytokem Prod. Inc., published Dec. 16, 1999; WO 00/56702 by Pfizer Inc., published Sep. 28, 2000; WO 00/76473 by Shiseido Co. Ltd., published Dec. 12, 2000; EP 997140 by L'Oreal SA, published May 3, 2000; JP 5221846 by Kunimasa Tomoji, published Aug. 31, 1993; JP 7242687 by Shiseido Co. Ltd., published Sep. 19, 1995; JP 7324023 by Itogawa H, published Dec. 12, 1995; JP 8012552 by Shiseido Co. Ltd., published Jan. 16, 1996; JP 8012554 by Shiseido Co. Ltd., published Jan. 16, 1996; JP 8012557 by Shiseido Co. Ltd., published Jan. 16, 1996; JP 8012560 by Shiseido Co. Ltd., published Jan. 16, 1996; JP 8012561 by Shiseido Co. Ltd., published Jan. 16, 1996; JP 8134090 by Fujisawa, published May 28, 1996; JP 8168378 by Kirinjo KK, published Jul. 2, 1996; JP 8277225 by Kansai Koso KK, published Oct. 22, 1996; JP 9002967 by Sanki Shoji KK, published Jan. 7, 1997; JP 9295927 by Yagi Akira, published Nov. 18, 1997; JP 10072330 by Kansai Kouso, published Mar. 17, 1998; JP 10081626 by Kamiyama KK, published Mar. 31, 1998; JP 10101543 by Kansai Kouso KK, published Apr. 21, 1998; JP 11071231 by Maruzen Pharm., published Mar. 16, 1999; JP 11079934 by Kyodo Nyugyo, published Mar. 23, 1999; JP 11246347 by Shiseido Co. Ltd., published Sep. 14, 1999; JP 11246344 by Shiseido Co. Ltd., published Sep. 14, 1999; JP 2000-080023 by Kanebo Ltd., published Mar. 21, 2000; JP 2000-095663 by Kose KK, published Apr. 4, 2000; JP 2000-159681 by Hai Tai Confectionary Co. Ltd., published Jun. 13, 2000; JP 2000-247907 by Kanebo Ltd., published Sep. 12, 2000; JP-9002967 by Sanki Shoji KK, published Jan. 7, 1997; JP-7206753 by Nikken Food KK, published Aug. 8, 1995; JP-5320025 by Kunimasa T, published Dec. 3, 1993; and JP-59157009 by Yakurigaku Chuou KE, published Sep. 6, 1984; among others.

For skin lightening, an active compound used in the present invention can also be used in combination with sun screens (UVA or UVB blockers) to prevent repigmentation, to protect against sun or UV-induced skin darkening, or to enhance their ability to reduce skin melanin and their skin bleaching action. For skin lightening, an active compound used in the present invention can also be used in combination with retinoic acid or its derivatives or any compounds that interact with retinoic acid receptors and accelerate or enhance the invention's ability to reduce skin melanin and skin bleaching action, or enhance the invention's ability to prevent the accumulation of skin melanin. For skin lightening, an active compound used in the present invention can also be used in combination with 4-hydroxyanisole. For skin lightening, the active compounds used in this invention can also be used in combination with ascorbic acid, its derivatives and ascorbic-acid based products (such as magnesium ascorbate) or other products with an anti-oxidant mechanism (such as resveratrol) which accelerate or enhance their ability to reduce skin melanin and their skin bleaching action.

A topically applied composition of the invention contains a pharmaceutically effective agent that inhibits FAS activity as described herein, and those ingredients as are necessary for use as a carrier. Non-limiting examples of such carriers are described in more detail below and may be found in International Patent Publication WO 00/62742, published Oct. 26, 2000, U.S. Pat. No. 5,691,380 to Mason et al., issued Nov. 25, 1997, U.S. Pat. No. 5,968,528 to Decker et al., issued Oct. 19, 1999, U.S. Pat. No. 4,139,619 to Chides, III, issued Feb. 13, 1979, and U.S. Pat. No. 4,684,635 to Orentreich et al., issued Aug. 4, 1987. Suitable pharmaceutical carriers are further described in *Remington's Pharmaceutical Sciences*, (1990) (supra) a standard reference text in this field.

The pharmaceutical compositions of the invention may also include other components. Such optional components should be suitable for application to keratinous tissue, that is, when incorporated into the composition, they are suitable for use in contact with human keratinous tissue without undue toxicity, incompatibility, instability, allergic response, and the like within the scope of sound medical judgment. In addition, such optional components are useful provided that they do not unacceptably alter the benefits of the FAS inhibitor and other active compounds of the invention. The *CTFA Cosmetic Ingredient Handbook* (1992) Second Edition, describes a wide variety of non-limiting cosmetic and pharmaceutical ingredients commonly used in the skin care industry, which are suitable for use in the compositions of the present invention. Examples of these ingredient classes include: abrasives, absorbents, aesthetic components such as fragrances, pigents, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, anti-foaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin-conditioning agents (e.g., humectants, including miscellaneous and occlusive), skin soothing and/ or healing agents (e.g., panthenol and derivatives (e.g., ethyl panthenol), aloe vera, pantothenic acid and its derivatives, allantoin, bisabolol, and dipotassium glycyffhizinate), skin treating agents, thickeners, and vitamins and derivatives thereof.

In addition to the pharmaceutically effective amount of an FAS inhibitor, the topical compositions of the present invention also comprise a dermatologically acceptable carrier. The phrase "dermatologically acceptable carrier," as used herein, means that the carrier is suitable for topical application to the skin, i.e., keratinous tissue, has good aesthetic properties, is compatible with the active agents of the present invention and any other components, and will not cause any safety or toxicity concerns. A safe and effective amount of carrier is from about 50% to about99.99%, preferably from about 80% to about 99.9%, more preferably from about 90% to about 98%, and most preferably from about 90% to about 95% of the composition.

The carrier utilized in the compositions of the invention can be in a wide variety of forms. These include emulsion carriers, including, but not limited to, oil-in-water, water-in-oil, water-in-oil-in-water, and oil-in-water-in-silicone emulsions, a cream, an ointment, an aqueous solution, a lotion or an aerosol. As will be understood by the skilled artisan, a given component will distribute primarily into either the water or oil/silicone phase, depending on the water solubility/dispersibility of the component in the composition.

Emulsions according to the present invention generally contain a pharmaceutically effective amount of an FAS inhibitor and a lipid or oil. Lipids and oils may be derived from animals, plants, or petroleum and may be natural or synthetic (i.e., man-made). Preferred emulsions also contain a humectant, such as glycerin. Emulsions will preferably further contain from about 1% to about 10%, more preferably from about 2% to about 5%, of an emulsifier, based on the weight of the carrier. Emulsifiers may be nonionic, anionic or cationic. Suitable emulsifiers are disclosed in, for example, U.S. Pat. No. 3,755,560 to Dickert et al., issued Aug. 28, 1973, and *McCutcheon's Detergents and Emulsifiers*, North American Edition, pp. 317–324 (1986).

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, most preferably about 5 centistokes or less. The emulsion may also contain an anti-foaming agent to minimize foaming upon application to the keratinous tissue. Anti-foaming agents include high molecular weight silicones and other materials well known in the art for such use.

One type of emulsion is a water-in-silicone emulsion. Water-in-silicone emulsions contain a continuous silicone phase and a dispersed aqueous phase. Preferred water-in-silicone emulsions of the present invention comprise from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase may contain a polyorganosiloxane oil. A preferred water-in-silicone emulsion system is formulated to provide an oxidatively stable vehicle for delivery of a pharmaceutically effective amount of an FAS inhibitor. The continuous silicone phase of these preferred emulsions comprises between about 50% and about 99.9% by weight of organopolysiloxane oil and less than about 50% by weight of a nonsilicone oil. In an especially preferred embodiment, the continuous silicone phase comprises at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and most preferably less than about 2%, by weight of the continuous silicone phase. These useful emulsion systems may provide more oxidative stability over extended periods of time than comparable water-in-oil emulsions containing lower concentrations of the polyorganosiloxane oil. Concentrations of non-silicone oils in the continuous silicone phase are minimized or avoided altogether so as to possibly further enhance oxidative stability of the active compound of the invention in the compositions. Water-in-silicone emulsions of this type are described in U.S. Pat. No. 5,691,380 to Mason et al., issued Nov. 25, 1997.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100 degrees Celsius. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes, which are known to those skilled in the art and commercially available.

The continuous silicone phase may contain one or more non-silicone oils. Concentrations of non-silicone oils in the continuous silicone phase are preferably minimized or avoided altogether so as to further enhance oxidative stability of the pharmaceutically effective agent in the compositions. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g. mineral oil, vegetable oils, synthetic oils. semisynthetic oils, etc.

Useful topical compositions of the present invention comprise from about 30% to about 90%, more preferably from about 50% to about 85%, and most preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore. The aqueous phase can be water, or a combination of water and one or more water soluble or dispersible ingredients. Nonlimiting examples of such optional ingredients include thickeners, acids, bases, salts, chelants, gums, water-soluble or dispersible alcohols and polyols, buffers, preservatives, sunscreening agents, colorings, and the like.

The topical compositions of the present invention typically comprise from about 25% to about 90%, preferably from about 40% to about 80%, more preferably from about 60% to about 80%, water in the dispersed aqueous phase by weight of the composition.

The water-in-silicone emulsions of the present invention preferably comprise an emulsifier. In a preferred embodiment, the composition contains from about 0.1% to about 10% emulsifier, more preferably from about 0.5% to about 7.5%, most preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with essential components of the composition, and provides the desired dispersion characteristics. Suitable emulsifiers include silicone emulsifiers, e.g., organically modified organopolysiloxanes, also known to those skilled in the art as silicone surfactants, non-silicon-containing emulsifiers, and mixtures thereof, known by those skilled in the art for use in topical personal care products.

Useful emulsifiers include a wide variety of silicone emulsifiers. These silicone emulsifiers are typically organically modified organopolysiloxanes, also known to those skilled in the art as silicone surfactants. Suitable emulsifiers are described, for example, in *McCutcheon's Detergents and Emulsifiers*, North American Edition (1986), published by Allured Publishing Corporation; U.S. Pat. No. 5,011,681, to Ciottie et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973.

Other preferred topical carriers include oil-in-water emulsions having a continuous aqueous phase and a hydrophobic, water-insoluble phase ("oil phase") dispersed therein. Examples of suitable carriers comprising oil-in-water emulsions are described in U.S. Pat. No. 5,073,371 to Turner et al., issued Dec. 17, 1991, and U.S. Pat. No. 5,073,372 to Turner et al., issued Dec. 17, 1991. An especially preferred oil-in-water emulsion, containing a structuring agent, hydrophilic surfactant and water, is described in detail hereinafter.

A preferred oil-in-water emulsion comprises a structuring agent to assist in the formation of a liquid crystalline gel network structure. Without being limited by theory, it is believed that the structuring agent assists in providing Theological characteristics to the composition which contribute to the stability of the composition. The structuring agent may also function as an emulsifier or surfactant. Preferred compositions of this invention comprise from about 0.5% to about 20%, more preferably from about 1% to about 10%, most preferably from about 1% to about 5%, by weight of the composition, of a structuring agent. The preferred structuring agents of the present invention are selected from the group consisting of stearic acid, palmitic acid, stearyl alcohol, cetyl alcohol, behenyl alcohol, stearic; acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

The preferred oil-in-water emulsions comprise from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water. Suitable surfactants include any of a wide variety of known cationic, anionic, zwitterionic, and amphoteric surfactants. See, *McCutcheon's Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973. The exact surfactant chosen depends upon the pH of the composition and the other components present. Preferred are cationic surfactants, especially dialkyl quaternary ammonium compounds, examples of which are described in U.S. Pat. No. 5,151,209 to McCall et al., issued Sep. 29, 1992; U.S. Pat. No. 5,151,210 to Steuri et al., issued Sep. 29, 1992; U.S. Pat. No. 5,120,532 to Wells et al., issued Jun. 9, 1992; U.S. Pat. No. 4,387,090 to Bolich, Jr., issued Jun. 7, 1983; U.S. Pat. No. 3,155,591 to Hilfer et al., issued Nov. 3, 1964; U.S. Pat. No. 3,929,678 to Laughlin et al., issued Dec. 30, 1975; and U.S. Pat. No. 3,959,461 to Bailey et al., issued May 25, 1976, and in *McCutcheon's Detergents & Emulsifiers* (North American edition 1979) M.C. Publishing Co.; and Schwartz, et al., *Surface Active Agents, Their Chemistry and Technology*, New York: lnterscience Publishers, 1949. Other useful cationic emulsifiers include amino-amides. A wide variety of anionic surfactants are also useful herein. See, e.g., U.S. Pat. No. 3,929,678, supra to Laughlin et al., issued Dec. 30, 1975. In addition, amphoteric and zwitterionic surfactants are also useful herein.

The preferred oil-in-water emulsion comprises from about 25% to about 98%, preferably from about 65% to about 95%, more preferably from about 70% to about 90% water by weight of the topical carrier.

The hydrophobic phase is dispersed in the continuous aqueous phase. The hydrophobic phase may contain water insoluble or partially soluble materials such as are known in the art, including but not limited to the silicones described herein in reference to silicone-in-water emulsions, and other oils and lipids such as described above in reference to emulsions.

The topical compositions of the subject invention, including, but not limited to, lotions and creams, may comprise a dermatologically acceptable emollient. Such compositions preferably contain from about 2% to about 50% of the emollient. As used herein, "emollient" refers to a material useful for the prevention or relief of dryness, as well as for the protection of the skin. A wide variety of suitable emollients are known and may be used herein. Sagarin, *Cosmetics, Science and Technology*, 2nd Edition, Vol. 1, p. 3243 (1972), which contains numerous examples of materials suitable as an emollient. A preferred emollient is glycerin. Glycerin is preferably used in an amount of from or about 0.001% to or about 20%, more preferably from or about 0.01% to or about 10%, most preferably from or about 0.1% to or about 5%, e.g., 3%.

Lotions and creams according to the present invention generally comprise a solution carrier system and one or more emollients. Lotions typically comprise from about 1% to about 20%, preferably from about 5% to about 10% of emollient; from about 50% to about 90%, preferably from about 60% to about 80% water; and a pharmaceutically effective amount of an FAS inhibitor described herein. A cream typically comprises from about 5% to about 50%, preferably from about 10% to about 20% of emollient; from about 45% to about 85%, preferably from about 50% to about 75% water; and a pharmaceutically effective amount of an FAS inhibitor described herein.

Ointments of the present invention may comprise a simple carrier base of animal or vegetable oils or semi-solid hydrocarbons (oleaginous); absorption ointment bases which absorb water to form emulsions; or water soluble carriers, e.g., a water soluble solution carrier. Ointments may further comprise a thickening agent, such as described in Sagarin, *Cosmetics, Science and Technology*, 2nd Edition, Vol. 1, pp. 72–73 (1972), and/or an emollient. For example, an ointment may comprise from about 2% to about 10% of an emollient; from about 0.1% to about 2% of a thickening agent; and a pharmaceutically effective amount of an FAS inhibitor described herein.

By way of non-limiting example, 1000 g of topical cream is prepared from the following types and amounts of ingredients: a skin-lightening effective amount of an FAS inhibitor, tegacid regular (150 g) (a self-emulsifying glyceryl monostearate from Goldschmidt Chemical Corporation, New York, N.Y.), polysorbate 80 (50 g), spermaceti (100 g), propylene glycol (50 g), methylparaben (1 g), and deionized water in sufficient quantity to reach 1000 g. The tegacid and spermaceti are melted together at a temperature of 70–80° C. The methylparaben is dissolved in about 500 g. of water and the propylene glycol, polysorbate 80, and 6-amino-1,2-dihydro-1-hydroxy-2-imino-4-piperidinopyrimidine free base are added in turn, maintaining a temperature of 75–80°

C. The methylparaben mixture is added slowly to the tegacid and spermaceti melt, with constant stirring. The addition is continued for at least 30 minutes with additional stirring until the temperature has dropped to 40–45° C. Finally, sufficient water is added to bring the final weight to 1000 g and the preparation stirred to maintain homogeneity until cooled and congealed.

By way of non-limiting example, 1000 g of a topical ointment is prepared from the following types and amounts of ingredients: a skin-lightening effective amount of an FAS inhibitor, zinc oxide (50 g), calamine (50 g), liquid petrolatum (heavy) (250 g), wool fat (200 g), and enough white petrolatum to reach 1000 g. Briefly, the white petrolatum and wool fat are melted and 100 g of liquid petrolatum added thereto. The pharmaceutically effective amount of an FAS inhibitor, zinc oxide, and calamine are added to the remaining liquid petrolatum and the mixture milled until the powders are finely divided and uniformly dispersed. The mixture is stirred into the white petrolatum, melted and cooled with stirring until the ointment congeals.

By way of non-limiting example, 1000 g of an ointment containing a pharmaceutically effective amount of an FAS inhibitor is prepared from the following types and amounts of ingredients: a skin-lightening effective amount of an FAS inhibitor, light liquid petrolatum (250 g), wool fat (200 g), and enough white petrolatum to reach 1000 g. Briefly, the pharmaceutically effective amount of the FAS inhibitor is finely divided and added to the light liquid petrolatum. The wool fat and white petrolatum are melted together, strained, and the temperature adjusted to 45–50° C. The liquid petrolatum slurry is added, and the ointment stirred until congealed.

By way of non-limiting example, 1000 ml of an aqueous solution containing a skin-lightening effective amount of an FAS inhibitor is prepared from the following types and amounts of ingredients: a pharmaceutically effective amount of an FAS inhibitor, polyethylene glycol 4000 (120 g) myristyl-γ-picolinium chloride (0.2 g), polyvinylpyrrolidone (1 g), and enough deionized water to reach 1000 milliliters. Briefly, the ingredients are dissolved in the water and the resulting solution is sterilized by filtration.

By way of non-limiting example, 1000 g of lotion containing a skin-lightening effective amount of an FAS inhibitor is prepared from the following types and amounts of ingredients: a pharmaceutically effective amount of an FAS inhibitor, N-methyl pyrolidone (40 g), and enough propylene glycol to reach 1000 g.

By way of non-limiting example, an aerosol containing a skin-lightening effective amount of an FAS inhibitor is prepared from the following types and amounts of materials: a pharmaceutically effective amount of an FAS inhibitor, absolute alcohol (4.37 g), dichlorodifluoroethane (DCFE) (1.43 g) and dichlorotetrafluoroethane (DCTFE) (5.70 g). Briefly, the pharmaceutically effective amount of an FAS inhibitor is dissolved in the absolute alcohol and the resulting solution filtered to remove particles and lint. This solution is chilled to about minus 30° C. Then, to this is added the chilled mixture of DCFE and DCTFE.

The compound that inhibits FAS activity (i.e., the active agent or ingredient) can also be administered orally in solid or semi-solid dosage forms, such as hard or soft-gelatin capsules, tablets, or powders, or in liquid dosage forms, such as elixirs, syrups, or suspensions. Additionally, the compound can also be administered parenterally, in sterile liquid dosage forms or in suppository form. The FAS inhibitors of the invention can also be administered rectally, intranasally, intravascularly, intramuscularly, etc.

Because in vivo use is contemplated, the composition is preferably of high purity and substantially free of potentially harmful contaminants, e.g., at least National Food (NF) grade, generally at least analytical grade, and preferably at least pharmaceutical grade. To the extent that a given compound must be synthesized prior to use, such synthesis or subsequent purification shall preferably result in a product that is substantially free of any potentially contaminating toxic agents that may have been used during the synthesis or purification procedures.

For oral administration, gelatin capsules or liquid-filled soft gelatin capsules can contain the FAS inhibitor and other active ingredient in powdered or liquid carriers, such as lactose, lecithin starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and to protect the tablet from the atmosphere, or enteric-coated for selective, targeted disintegration in the gastrointestinal tract. Liquid dosage forms for oral administration can contain coloring and/or flavoring to increase patient acceptance.

In general, for parenteral solutions, sterile water, oil, saline, aqueous dextrose (glucose), polysorbate and related sugar solutions and glycols such as propylene glycol or polyethylene glycols are suitable carriers for a useful FAS inhibitor. Solutions or emulsions for parenteral administration preferably contain about 5–15% polysorbate 80 or lecithin, suitable stabilizing agents and, if necessary, buffer substances. Antioxidizing agents such as, but not limited to, sodium bisulfite, sodium sulfite, or ascorbic acid, either alone or combined, are suitable stabilizing agents. Also useful are citric acid and its salts, and sodium EDTA. In addition, parenteral solutions can contain preservatives including, but not limited to, benzalkonium chloride, methyl- or propyl-paraben, and chlorobutanol.

Thus, the invention further provides a method of making compositions for lightening skin comprising admixing a skin-lightening effective amount of an FAS inhibitor with a pharmaceutically or cosmetically acceptable carrier.

As will be understood by those in the art in view of this disclosure, the compositions of the invention may be provided in the form of a kit. Kits of the invention comprise one or more specific compositions of the invention that lighten skin by inhibiting FAS activity. The kit may also comprise additional agents that inhibit melanin production or lighten the skin, as well as a pharmaceutically or cosmetically acceptable carrier. Optionally, the kit further comprises printed instructions as a label or package insert directing the use of such compositions to lighten skin. The compounds are preferably provided in a sterile container designed to prevent contamination, minimize evaporation or drying of the composition, etc. The compounds may or may not be provided in a preset dose or usage amount.

The invention having been described, the following examples directed to the use of such compositions to lighten skin are offered by way of illustration and not limitation.

EXAMPLES

Example 1

Assay for Melanin Production After Cerulenin Treatment

Melan-a melanocytes (α/α, P/P), an immortalized melanocyte line derived from C57BLI6J mice wild type at the p locus (Bennett et al. (1987), *Int. J. Cancer* 39:414–418), were incubated in Dulbecco's modification of Eagle's medium (DMEM: 10% fetal calf serum, 2 mM L-glutamine, 1 mM sodium pyruvate, 1% MEM non-essential amino acids 100×, 50µ/L penicillin, 50 µg/L streptomycin). Immediately before using the medium, tetradecanoyl phorbol acetate (TPA) was added at 200 nM. Cells were seeded in T-25 flasks with 4×10⁴ cells/ml×4.5 ml/flask (10–20% confluent) and were grown at 37° C. with 5% $CO_2$. Twenty-four hours later, a compound to be tested (diluted in 0.5 ml media) was added to the media. Forty-eight hours after the addition of drug, both the media and drug were changed. Cells were harvested after an additional 48 or 72 hours (100% confluent).

In harvesting the cells, the reagents and cells were kept at 4° C. Briefly, the media was removed from the cells, and one milliliter of media was reserved if needed for the tyrosinase assay. The cells were then rinsed with approximately 500 µl cold 1×phosphate buffered saline (PBS) until the PBS rinse was clear. Cold extraction buffer (50 mM Tris, pH 7.5, 2 mM EDTA, 150 mM NaCl, and 1% Triton x-100 (Sigma, St. Louis, Mo.) (500 µl)) was added, and the sample was allowed to incubate on ice for a few minutes or until cells began to peel off the bottom of the flask. After tapping the flask to encourage the cells to fall off, the 500 µl of the extraction buffer/cells were removed and placed in a microfuge tube. After spinning the sample for 5 minutes at 14,000×g at 4° C., the supernatant was removed and saved in a microfuge tube for the protein assay (and tyrosinase assay, if necessary). At this point, the cell pellets may be stored at 4° C. overnight or at −20° C. for longer periods before assaying for melanin.

In order to assay for melanin, 300–500 µl of ethanol/ether (1:1) was added to each pellet of cells. The sample was vortexed and allowed to stand for approximately 10 minutes or until precipitated protein was visible in the solvent. If necessary, pellets were gently crushed with a microfuge tube pestle. Care was taken not to break the pellet(s) into many small pieces which would have made removing the solvent (and leaving melanin behind) difficult. Using a glass pipette, the solvent/protein was removed, being careful not to remove melanin. The extraction steps were repeated, and the pellets allowed to dry. Next, 250 µl of 2 N NaOH in 20% dimethylsulfoxide (DMSO) was added to each microfuge tube. The samples were heated at 60–70° C. until the melanin was completely dissolved. For each sample tested, 200 µl of the NaOH/melanin solution was transferred to a 96-well plate. 2 N NaOH in 20% DMSO was used as a blank, and the samples were read at a wavelength of 490 nm. The data were reported as absorbance of melanin per protein calculated for the total sample.

In order to determine the effects of cerulenin on melanin production, melan-a melanocytes were incubated in the presence of 0.05:9, 1:9, 0.5:9, or 5:9 cerulenin (Sigma, St. Louis, Mo.) as outlined above. In addition, cells were also separately treated with 300 µM 1-phenyl-2-thiourea (PTU) (Sigma, St. Louis, Mo.), a direct inhibitor of tyrosinase and 100 µM isobutylmethylxanthine (IBMX) (Sigma, St. Louis, Mo.), a phosphodiesterase inhibitor, or not treated with any drug.

The results, as presented in FIG. 1, indicate that cerulenin decreases pigmentation in melan-a melanocytes an average of 50% at 3 µM.

Example 2

Assay For Melanin Production After Treatment With α-Methylene-γ-butryolactone The effects of other FAS inhibitors on melanin production is tested by incubating melan-a melanocytes in the presence of 0.1 µM, 1.0 µM, 10.0 µM, or 100.0 µM α-methylene-γ-butyrolactone (Sigma, St. Louis, Mo.) following the procedure outlined above in Example 1. In addition, cells are also separately treated with 20 µM IMP (Sigma, St. Louis, Mo.), 300 µM PTU (Sigma, St. Louis, Mo.), 100 µM IBMX (Sigma, St. Louis, Mo.), or are untreated.

It is expected that melanin production will also be reduced in the treated cells.

Example 3

Assay For Melanin Production After Treatment With Thiolactomycin

The effects of other FAS inhibitors on melanin production is tested by incubating melan-a melanocytes in the presence of 0.1 µM, 1.0 µM, 10.0 µM, or 100.0 µM thiolactomycin following the procedure outlined above in Example 1. In addition, cells are also separately treated with 20 µM IMP (Sigma, St. Louis, Mo.), 300 µM PTU (Sigma, St. Louis, Mo.), 100 µM IBMX (Sigma, St. Louis, Mo.), or are untreated.

It is expected that melanin production will also be reduced in the treated cells.

Equivalents

Those skilled in the art will recognize, or be able to ascertain, using no more than routine experimentation, many equivalents to the specific embodiments of the invention described herein. Such equivalents are intended to be encompasssed by the following claims.

What is claimed is:

1. A method of decreasing melanin synthesis in a melanocyte, comprising contacting the melanocyte with a melanin synthesis inhibiting amount of a fatty acid synthase (FAS) inhibitor, thereby reducing melanin synthesis in the melanocyte.

2. The method of claim 1, wherein the FAS inhibitor is cerulenin or a pharmaceutically acceptable salt or solvate thereof.

3. The method of claim 1, wherein the FAS inhibitor is an α-methylene-γ-butyrolactone or a pharmaceutically acceptable salt or solvate thereof.

4. The method of claim 1, wherein the FAS inhibitor is thiolactomycin or a pharmaceutically acceptable salt or solvate thereof.

5. A method of lightening skin, comprising contacting the skin of a patient in need thereof with a skin-lightening effective amount of a fatty acid synthase (FAS) inhibitor.

6. The method of claim 5, wherein the FAS inhibitor is cerulenin or a pharmaceutically acceptable salt or solvate thereof.

7. The method of claim 5, wherein the FAS inhibitor is an α-methylene-γ-butyrolactone or a pharmaceutically acceptable salt or solvate thereof.

8. The method of claim 5, wherein the FAS inhibitor is thiolactomycin or a pharmaceutically acceptable salt or solvate thereof.

9. A kit comprising a sterile container comprising a skin-lightening effective amount of a compound that inhibits FAS activity.

10. The kit of claim 9, further comprising a set of printed instructions directing the use of the compound to lighten skin.

11. A method of making a skin-lightening composition comprising combining a skin lightening effective amount of an FAS inhibitor with a pharmaceutically or cosmetically acceptable carrier.

* * * * *